United States Patent [19]

Keener et al.

[11] Patent Number: 5,677,494
[45] Date of Patent: Oct. 14, 1997

[54] METHOD FOR HIGH STRAIN-RATE TESTING OF SPECIMENS

[75] Inventors: Steven G. Keener, Trabuco Canyon; Charles P. Thrash, Anaheim; John T. Mecklenburg, Lakewood, all of Calif.

[73] Assignee: McDonnell Douglas Corporation, Huntington Beach, Calif.

[21] Appl. No.: 609,599

[22] Filed: Mar. 5, 1996

[51] Int. Cl.$^6$ .................................................. G01N 3/32
[52] U.S. Cl. .......................... 73/810; 73/760; 73/797
[58] Field of Search ........................... 73/12.01, 12.09, 73/760, 794, 797, 810, 831, 834, 844, 845, 852, 856

[56] References Cited

U.S. PATENT DOCUMENTS

| | | | |
|---|---|---|---|
| 3,158,048 | 11/1964 | Bollar | 73/12.01 |
| 3,693,421 | 9/1972 | Karper et al. | 73/12.01 |
| 3,714,821 | 2/1973 | Gilley | 73/797 |
| 4,845,995 | 7/1989 | Kaste et al. | 73/794 |
| 5,279,166 | 1/1994 | Ward et al. | 73/794 |

OTHER PUBLICATIONS

Declaration of Steven G. Keener, dated Apr. 10, 1996.

*Primary Examiner*—Richard Chilcot
*Assistant Examiner*—Max H. Noori
*Attorney, Agent, or Firm*—Bell, Seltzer, Park & Gibson, P.A.

[57] ABSTRACT

A mechanical impact test is performed using an incremental mechanical loading apparatus having a loading head movable in a first direction and in a second direction opposite to the first direction, and a stationary cross piece. A starter specimen is mounted between the loading head and the stationary cross piece, such that the starter specimen extends in the first direction from the loading head and the movement of the loading head in the second direction applies a tensile load to the starter specimen. A test specimen is mounted to the loading head such that a mechanical reaction force generated by the breaking of the starter specimen is imparted from the starter specimen to the test specimen. To perform the test, the loading head of the incremental mechanical loading apparatus is moved in the second direction such that the starter specimen is loaded to failure, with the result that the failure of the starter specimen causes the application of an impact force to the test specimen.

19 Claims, 6 Drawing Sheets

METHOD FOR HIGH STRAIN-RATE TESTING OF SPECIMENS

BACKGROUND OF THE INVENTION

This invention relates to mechanical testing, and, more particularly, to a mechanical testing approach for applying high strain-rate loadings to specimens to simulate impact and other types of rapidly occurring failure events.

Structural materials and components are selected for service applications with consideration for their responses under different rates of loading. Laboratory techniques are often used to test the materials and components under conditions that approximate those expected in service. The resulting information is utilized in the process of improving designs and materials, and selecting between available materials for specific applications. The present invention deals with the test measurement of the behavior of materials, components, and structural elements.

The performance of a material or a component in a specific structural application depends upon the nature of the loading or strain that is imposed during service. One of the factors that determines the nature of the loading and the resulting performance is the rate at which the load or strain is imposed, because the behavior of many materials varies widely with such loading rate. For example, a great deal of the conventional tensile testing of materials is conducted with an applied rate of strain loading on the order of 0.01–10 inches per inch per minute. Creep testing is accomplished at strain rates on the order of thousandths of a percent per minute, and impact testing is accomplished at strain rates on the order of thousands of percent per minute.

The behavior of materials and components at high loading rates or high strain rates is of interest in situations where an impact load may be applied during service, such as can occur in an accident. Conventional mechanical test machines of the well-known "Instron" and "MTS" types do not have the capability to produce the high strain rates characteristic of impact-type loading. Some test devices that produce high loading rates have been developed, but they tend to be highly specialized, not readily adapted to other uses, and costly to build and operate. The most popular tests for determining the properties of metals at high strain rates require specific configurations and sizes of test specimens and are not adaptable to other types of specimens or to structural components. Moreover, in some cases the strain rate is fixed, and cannot be readily varied.

There is a need for an improved, lower cost approach for the mechanical testing of materials and components at high loading rates and/or high strain rates. The present invention fulfills this need, and further provides related advantages.

SUMMARY OF THE INVENTION

The present invention provides a general purpose test apparatus and method for performing the mechanical testing of materials and components at high strain rates. The testing is quickly and easily performed. The approach is operable with a wide range of specific test types and specimen configurations. It permits the applied strain rate to be varied over a wide range, without changing the specimen size or configuration. The test apparatus is based upon the use of a widely available configuration of test machine.

In accordance with the invention, a test method comprises the steps of providing an incremental mechanical loading apparatus having a movable loading head and a stationary cross piece. A starter specimen is mounted between the loading head and the stationary cross piece. The starter specimen extends in a first direction from the loading head, such that the movement of the loading head in a second direction (opposite to the first direction) applies a tensile force to the starter specimen. A test specimen is mounted in a fixture on the loading head, such that a mechanical reaction force generated by the breaking of the starter specimen is transmitted from the starter specimen to the test specimen. The loading head of the incremental mechanical loading apparatus is moved in the second direction such that the starter specimen is loaded to failure. The failure of the starter specimen causes the application of an impact force to the test specimen.

In one embodiment, a test method comprises the steps of providing an incremental mechanical loading apparatus having a movable crosshead, mounting an unloaded starter specimen to the loading apparatus in a manner such that the starter specimen may be loaded to failure by the movable crosshead, and mounting a test specimen to the loading apparatus. The test specimen is mounted such that it is not loaded as the starter specimen is loaded prior to failure of the starter specimen, but such that the test specimen is loaded only after the starter specimen has been loaded to failure. Lastly, the starter specimen is loaded to failure using the movable crosshead. Energy released by the failure of the starter specimen is in turn used to load the test specimen to failure.

The incremental loading apparatus preferably comprises an incremental mechanical loading apparatus, including an incremental loading apparatus frame having a stationary cross piece and two parallel side supports extending from the stationary cross piece. There is a loading head supported between the two side supports and movable in a first direction parallel to the side supports and toward the stationary cross piece, and in a second direction opposite to the first direction. The loading head has a first side facing in the first direction and a second side facing in the second direction. The apparatus further includes a starter specimen first grip having a flange engaged to the loading head, a starter specimen second grip attached to the stationary cross piece, a test specimen frame supported on the second side of the loading head, and a test specimen first loading fixture engaged to the test specimen frame. An optional inertial mass, whose value may be varied to alter the strain rate applied to the test specimen, is positioned in load-transmitting mechanical communication with the test specimen first grip. A test specimen second loading fixture is engaged to the inertial mass, the test specimen second loading fixture being disposed such that a test specimen may be mounted between the test specimen first loading fixture and the test specimen second loading fixture. As will be discussed in the Detailed Discussion, an apparatus of this type is readily built using as a basis a conventional test machine, which otherwise has the capability only for low strain rate testing such as 0.01–10 inches per inch per minute, that is available in most materials and structures testing laboratories throughout the world. Thus, the capabilities of the standard machine are enlarged to permit high strain-rate testing of many materials and component configurations.

In this approach, the loading of the starter specimen permits energy to be stored in a way that later allows its rapid and controlled release into the test specimen. As the starter specimen is loaded toward failure, it is highly strained from the load applied by the loading head, which results in a large amount of energy being stored. When the starter specimen breaks, this stored energy is released as a recoil that is transmitted as an impact loading into the inertial mass (when present) and thence into the test specimen fixturing and the test specimen. The energy and strain-rate characteristics of the loading of the test specimen are controllable by the size of the starter specimen (i.e., the total force required to load it to failure) and the mass of the inertial mass. The larger the inertial mass, the slower the rate of loading of the test specimen due to the higher rate of energy dissipation imposed. This controllability of the strain rate allows detailed comparative studies of the behavior of the test specimen under high-rate loading and conventional, lower rates of loading.

The present approach can be used with a wide variety of test fixturing and test specimen types. Conventional tensile and shear tests can be performed over a wide range of strain rates, including but not limited to high strain rates. Tests of structural components can be performed in shear or tension. Fasteners, such as rivets, installed between structural elements, such as plates, are tested in their as-installed state. Other types of mechanical and metallurgical joints are also readily tested.

The present invention thus provides an improved testing device and a test method that are flexible in approach for high strain-rate testing, and permit the use of many types of specific tests. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
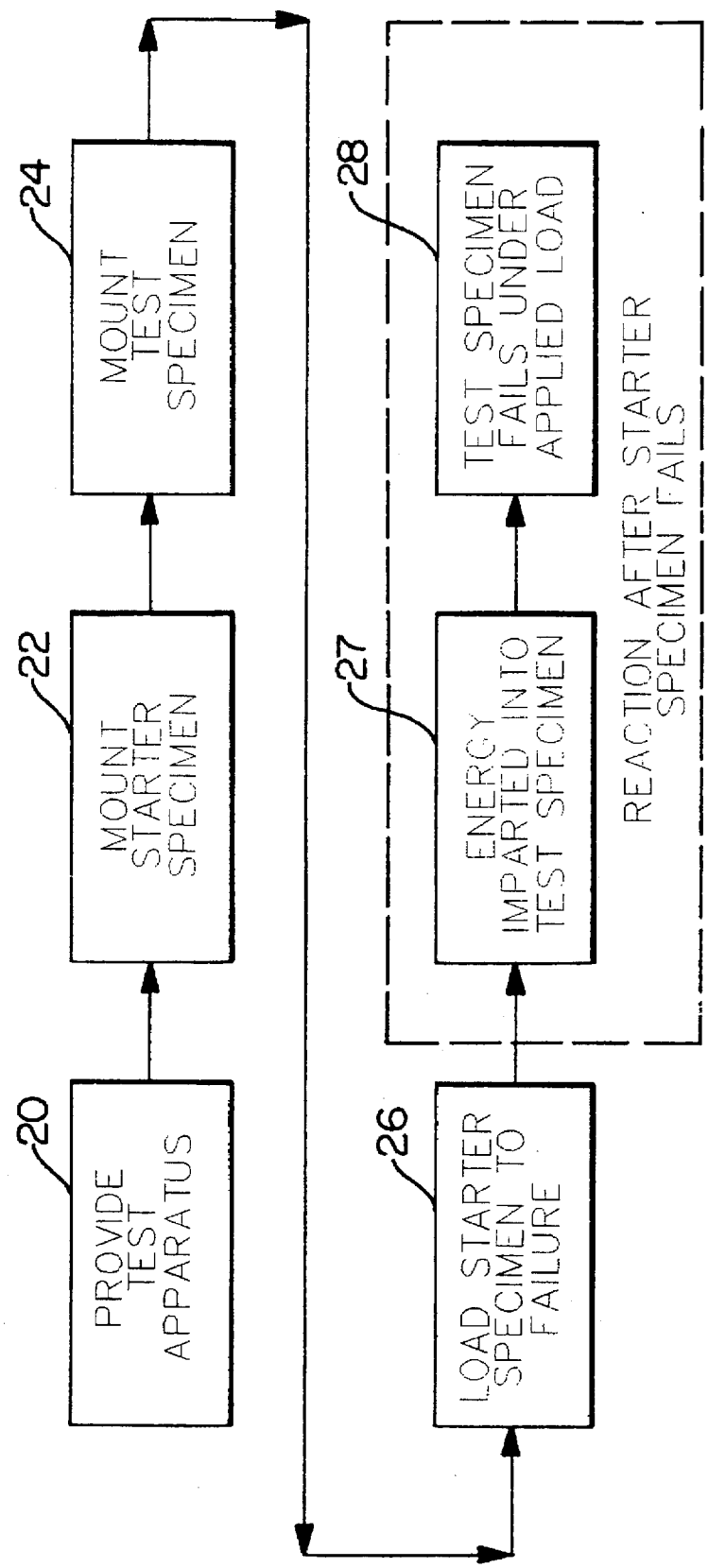
FIG. 1 is a block diagram of the steps of a test method according to the invention.
Figure 2A:
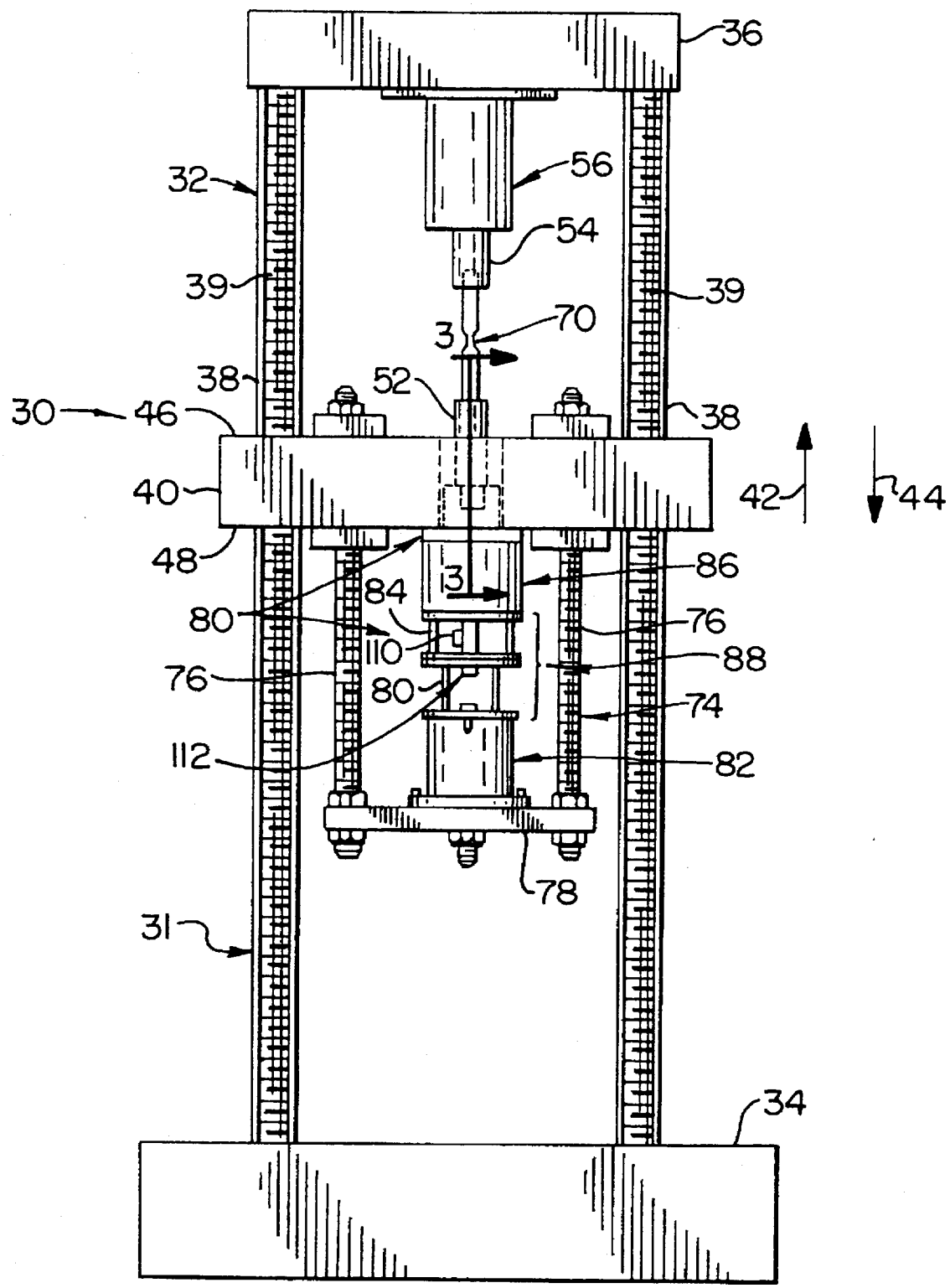
FIG. 2A is a schematic elevational view of a first embodiment of the apparatus.
Figure 2B:
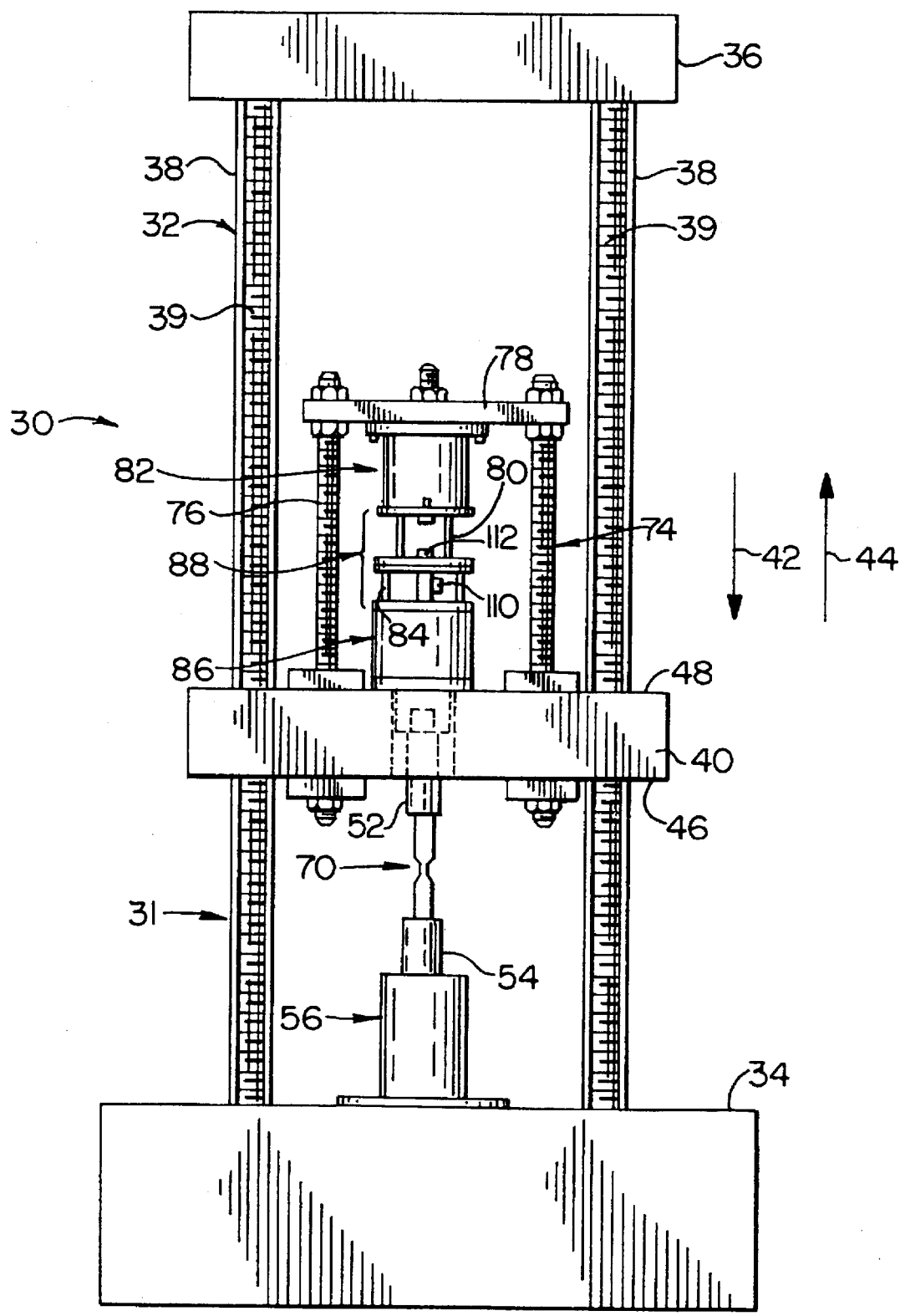
FIG. 2B is a schematic elevational view of a second embodiment of the apparatus.

FIG. 1 depicts an approach to mechanical testing conducted according to the invention. A mechanical test apparatus is provided, numeral 20. FIG. 2A and 2B depict two embodiments of such a mechanical test apparatus 30. These embodiments are similar, except that in the embodiment of FIG. 2A the test fixture is positioned below the loading cross head of the test apparatus and in FIG. 2B the test fixture is positioned above the loading cross head. Where the elements of structure are the same in FIGS. 2A and 2B, except for being inverted in some instances, the same reference numerals are applied and the description of the FIG. 2A embodiment applies to FIG. 2B as well, except as indicated in parentheses.

The test apparatus 30 includes a loading machine of the incremental loading type, meaning that a loading is applied to a specimen with a continuous, relatively slow rate of increase in the load or the strain applied to the specimen. Such an incremental loading machine 31, preferably of the type manufactured by the Instron Company, Canton, Mass., and termed in the art an "Instron"-type load machine, is widely available in materials and structures testing laboratories throughout the world. The preferred Instron-type load machine is the 4500 series, specifically the model 4507, or the model 1125. This incremental loading machine 31 and its equivalents, while highly useful for relatively slow loading of specimens, are not suitable in its commercially available form for rapid or impact loading of specimens.

The incremental loading machine 31 includes an incremental loading apparatus frame 32 having a stationary lower cross piece 34, a stationary upper cross piece 36, and two parallel side rails 38 extending between the cross pieces 34 and 36. Two parallel, externally threaded screw drives 39 also extend between the cross pieces 34 and 36, with a driving motor (not visible) for the screw drives 39 within the lower cross piece 34. (The side rails 38 and the screw drives 39 together constitute the side supports of the test apparatus.) A loading cross head 40 extends transversely between the two screw drives 39. The loading cross head 40 includes corresponding internal screw threads that engage the screw drives 39. The loading cross head 40 is controllably driven in a first direction 42 (up in FIG. 2A, down in FIG. 2B) parallel to the side rails 38 or an opposite second direction 44 by appropriate rotation of the screw drives 39. The loading cross head has a first side 46 facing in the first direction 42 and a second side 48 facing in the second direction 44.

The test apparatus 30 further includes a specialty test setup having a generally cylindrical symmetrical starter specimen first grip 52 extending upwardly (downwardly in FIG. 2B) through the loading cross head 40. A starter specimen second grip 54 extends downwardly (upwardly in FIG. 2B) from the upper cross piece 36 (lower cross piece 34 in FIG. 2B), with a starter specimen load cell 56 located in series between the second grip 54 and the upper cross piece 36 (lower cross piece 34 in FIG. 2B) to measure the load applied through the grips 52 and 54. The starter specimen load cell 56 provides load-sensing instrumentation for a starter specimen 70 engaged in series between the grips 52 and 54, and other instrumentation such as strain gages or an extensometer can also be provided.

Figure 3:
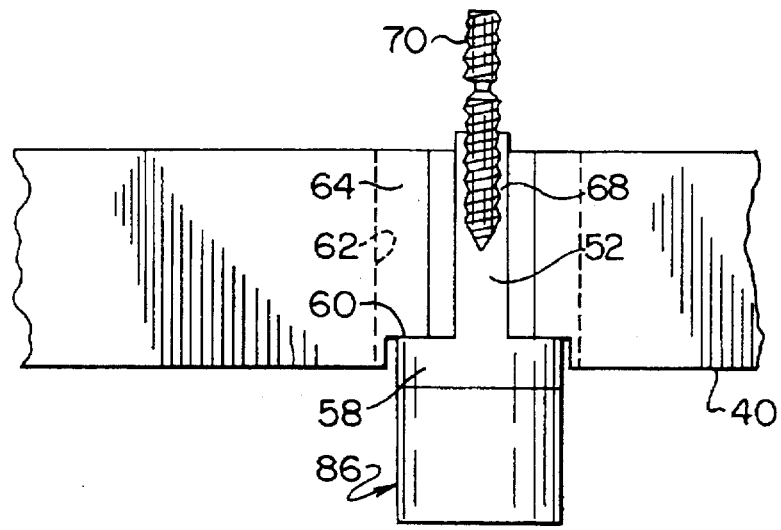
FIG. 3 is a sectional view of a detail of the apparatus of FIG. 2, taken along lines 3—3 of FIG. 2A.

The starter specimen first grip 52 is engaged to the loading cross head 40 in the manner illustrated in FIG. 3 (for the embodiment of FIG. 2A). The starter specimen first grip 52 has a flange 58 extending radially outwardly therefrom at its lower end. The flange 58 engages a downwardly facing shoulder 60 in the interior (or exterior) of the loading cross head 40. The commercial Instron machine has a loading cross head 40 with a bore 62 therein. The shoulder 60 is formed on an optional bore insert 64 that is bolted into the bore 62.

The starter specimen first grip 52 has an upwardly extending portion 68 above the flange 58. The flange 58 rests on the shoulder of the cross head 40 and is preferably threaded to engage an optional inertial mass 86 below (above in FIG. 2B) the loading cross head 40, when present, whose structure and function will be discussed subsequently. The upwardly extending portion 68 is threaded or otherwise configured at its upper end to engage the starter specimen 70. The starter specimen second grip 54 is threaded to engage the opposite end of the starter specimen 70. The starter specimen 70 is preferably a notched tensile bar configured to fail instantaneously at a specific applied load. The design of notched tensile bars to fail at a specific applied load is known in the art. For a specific material of construction and size of the starter specimen, such as a specific steel, the notched failure load is readily determined by standard calculations and verified by testing.

Returning to the discussion of FIG. 2, a stationary test specimen frame 74 extends downwardly (upwardly in FIG. 2B) from the loading cross head 40. The test specimen frame 74 includes four side supports 76 affixed to the loading cross head 40 and extending from the second side 48, and a frame cross piece 78 affixed to the four side supports 76 at a location remote from the loading cross head 40. A test specimen first loading fixture 80 is engaged to the frame cross piece 78, preferably through an intermediate test specimen impact load cell 82. (A preferred load cell 82 is the Series 200 Quartz Impact Force Sensor available from PCB Piezotronics, Buffalo, N.Y.) The test specimen piezoelectric impact load cell 82 provides instrumentation for the test specimen. Other instrumentation such as strain gages or an extensometer may also be provided as appropriate.

A test specimen second loading fixture 84 is affixed to the optional inertial mass 86, which in turn is affixed to a lower end of the flange 58. When the test is performed, the test specimen second loading fixture 84 is rapidly driven downwardly (upwardly in FIG. 2B) when the starter specimen 70 breaks. The mass of the inertial mass 86 in different tests may be selectively varied to achieve different loading rates to the test specimen. The test specimen first loading fixture 80, the test specimen second loading fixture 84, and a test specimen therein form a test specimen assembly fixture 88.

Figure 4:
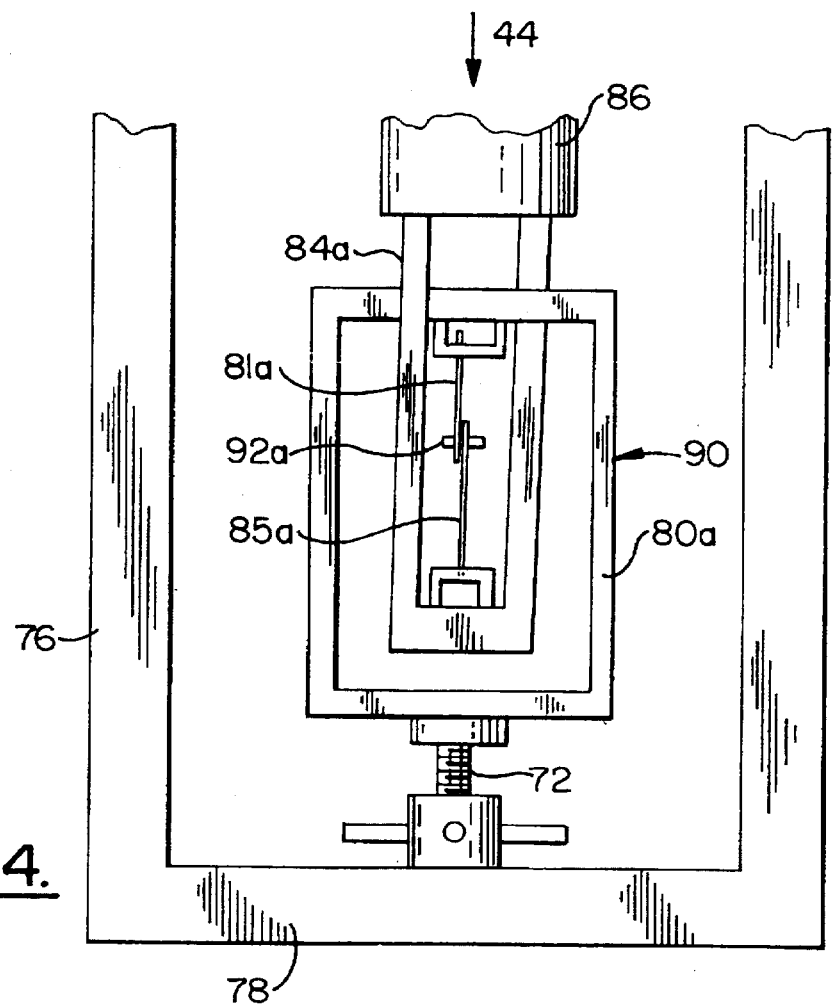
FIG. 4 is a schematic elevational view of a fastener shear-testing future and test specimen.
Figure 5:
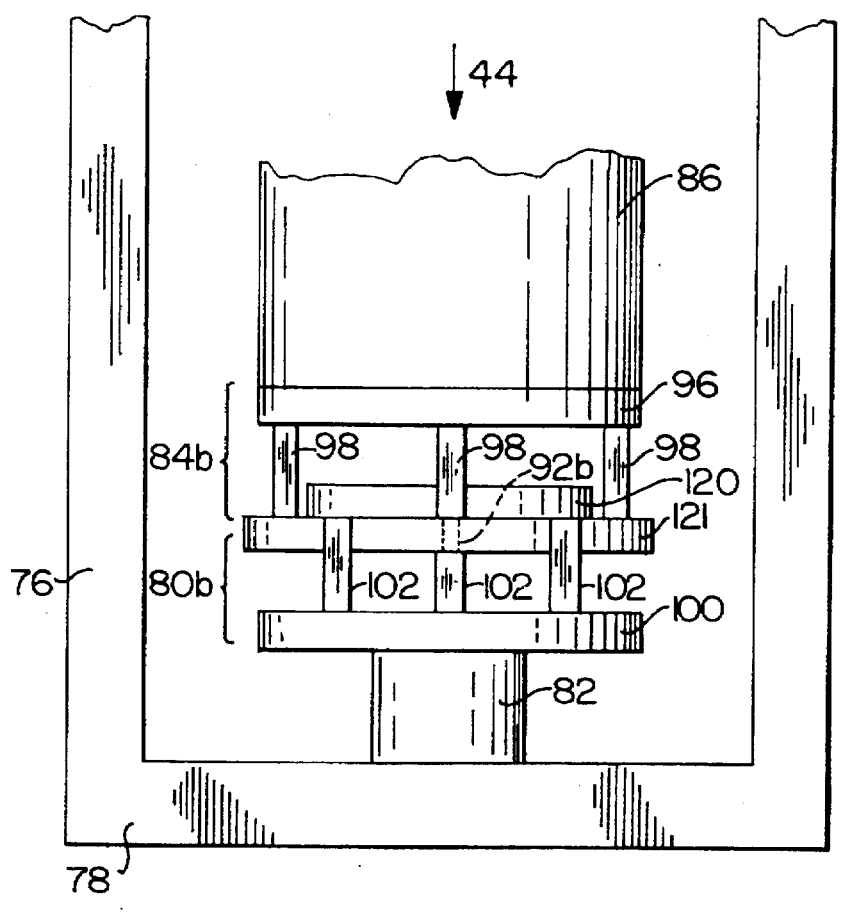
FIG. 5 is a schematic elevational view of a fastener tension-testing fixture and specimen.
Figure 6:
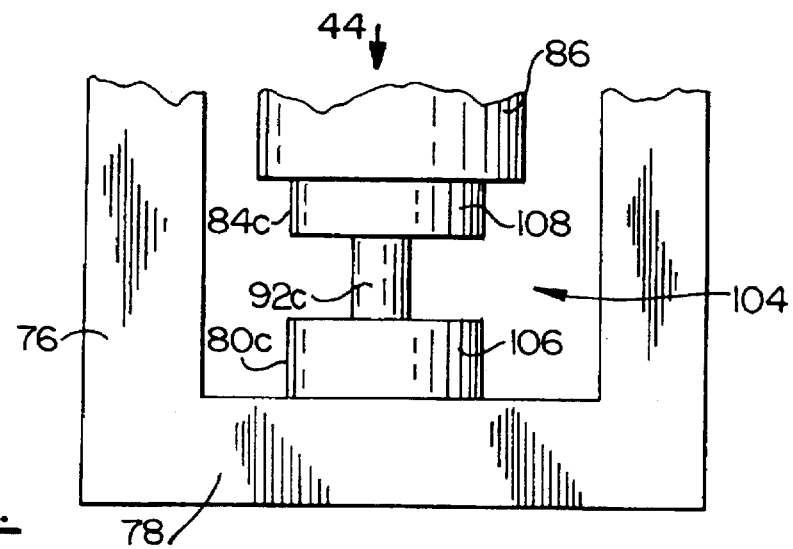
FIG. 6 is a schematic elevational view of a compression-testing fixture and specimen.

An important virtue of the present invention is that a wide range of test specimen assembly fixture arrangements may be used. FIGS. 4-6 illustrate three different test specimen assembly fixture arrangements used in embodiment of FIG. 2A by way of example, with the test specimen load cell 82 omitted for clarity in illustration of the test specimen assembly fixtures. These three test specimen assembly fixtures are chosen to show that the present approach permits high-rate impact test loading in shear (FIG. 4), tension (FIG. 5), or compression (FIG. 6), the three most important loading modes in such testing, and also of components (FIGS. 4 and 5) and materials (FIG. 6).

In a shear test specimen assembly fixture 90 of FIG. 4, the test specimen first loading fixture 80a is an upwardly extending first yoke with a plate 81a extending downwardly from its upper end. The test specimen second loading fixture 84a is a downwardly extending second yoke with a plate 85a extending upwardly from its lower end and oriented at an angle to the first yoke to fit between its legs. Only a single upwardly extending plate 85a is shown, resulting in a single shear test. Two upwardly extending plates, one on each side of the downwardly extending plate 81a, would be used in a double shear test. A test specimen 92 in this case is a mechanical fastener 92a extending between the plates 81a and 85a. When the test specimen second loading fixture 84a is driven downwardly in direction 44 during performance of a test, the fastener 92a is loaded in shear between the two plates. The test specimen 92 could be any other element which is to be loaded in shear, such as a metallurgical joint (i.e., a weldment) or adhesive bond such as used in composite materials between the two plates, a materials shear test specimen, or another type of fastener such as a rivet.

In a tensile test specimen assembly fixture 94 of FIG. 5, the test specimen second loading fixture 84b includes an upper plate 96 supported from the inertial mass 86 by four legs 98. The test specimen first loading fixture 80b includes a lower plate 100 supported from the frame cross piece 78 by four legs 102 (which are similar to, but rotated 90 degrees to the four legs 98). The test specimen 92 in this case is a rivet 92b joining two plates 120 and 121. When the upper plate 96 is driven downwardly in the second direction 44 after the starter specimen 70 breaks during a test procedure, by the downward movement of the inertial mass 86 (or in its absence the flange 58), a tensile force is applied to the rivet 92b. The rivet 92b is loaded in tension in an attempt to fail the rivet and move the plates 120 and 121 apart. The failure of a rivet by this test of FIG. 5, and the shear failure of a rivet using the approach of FIG. 4 are of particular interest to the inventors, because the failure of fasteners such as rivets in an aircraft fuselage skin in a progressive failure mode leads to a massive loss of structural integrity of the fuselage skin. The test specimen 92 of FIG. 5 could be any other element which is to be loaded in tension, such as a weldment between the two plates, a material's tensile specimen, an adhesive bond between two components, or another type of component such as a bolt.

In a compressive test specimen assembly fixture 104 of FIG. 6, the test specimen first loading fixture 80c is a lower compression plate 106, and the test specimen second loading fixture 84c is an upper compression plate 108. A materials compression test specimen 92c is positioned between the two plates 106 and 108. When the test specimen second loading fixture 84c is driven downwardly in the second direction 44 during a test, the compression test specimen 92c is rapidly loaded in compression. The test specimen 92 could be any other element which is to be loaded in compression, such as a bolt or rivet or other material.

Returning to the discussion of FIG. 1, the starter specimen 70 is mounted in the test apparatus 30 to extend between the grips 52 and 54, numeral 22. The test specimen 92 is mounted in the selected test specimen assembly fixture 88, numeral 24. The starter specimen 70 is not preloaded to a high load value, but only to a load required to eliminate play in the setup The lower frame cross piece 78 is hand tightened to preload the test specimen 92, as shown for example with the preload screw thread 72 of FIG. 4.

The incremental loading apparatus frame 32 is operated to move the loading cross head in the second direction 44, numeral 26, typically at a rate of about 0.1 inch per minute. The load on the starter specimen 70 is thereby gradually increased. As the load on the starter specimen is increased, energy is, in turn, stored in the starter specimen 70. At the point where sufficient load is applied to the starter specimen 70, the starter specimen instantaneously breaks, numeral 26. The energy stored in the starter specimen is released in a rapid recoil in the second direction 44. This recoil energy is imparted as a rapid movement in the second direction 44 to the inertial mass 86 and thence to the test specimen second loading fixture 84, or directly transferred to the test specimen second loading fixture 84 if no inertial mass 86 is provided. The test specimen 92 is loaded, numeral 27, typically to failure, numeral 28, by this rapid energy transfer or impact loading.

The total mass of the inertial mass 86 directly affects the rate of loading of the test specimen 92. Where the inertial mass 86 is selected to be absent or small, the test specimen 92 is loaded relatively rapidly. Where the inertial mass 86 is selected to be large, the test specimen 92 is loaded relatively slowly. It has been determined that the use of a sufficiently large inertial mass permits the test specimen 92 to be loaded at a rate comparable with that experienced in conventional low strain-rate, quasi-static testing. A comparison of the results of different testing load rates is thereby permitted. Additionally, an understanding of the deformation and/or failure behavior of the test specimen 92 as a function of loading rate is achieved by testing a series of identical test specimens 92 and test fixtures 88, using a different inertial mass 86 for each test. An accelerometer 110, a load cell, or other suitable measuring device mounted to the test specimen 92 or test fixture 88 provides a measure of the rate of load application versus time history. Strain measuring instrumentation 112 such as a strain gage or extensometer affixed to the test specimen 92 provides a measure of the applied rate of strain or deformation of the test specimen.

Figure 7:
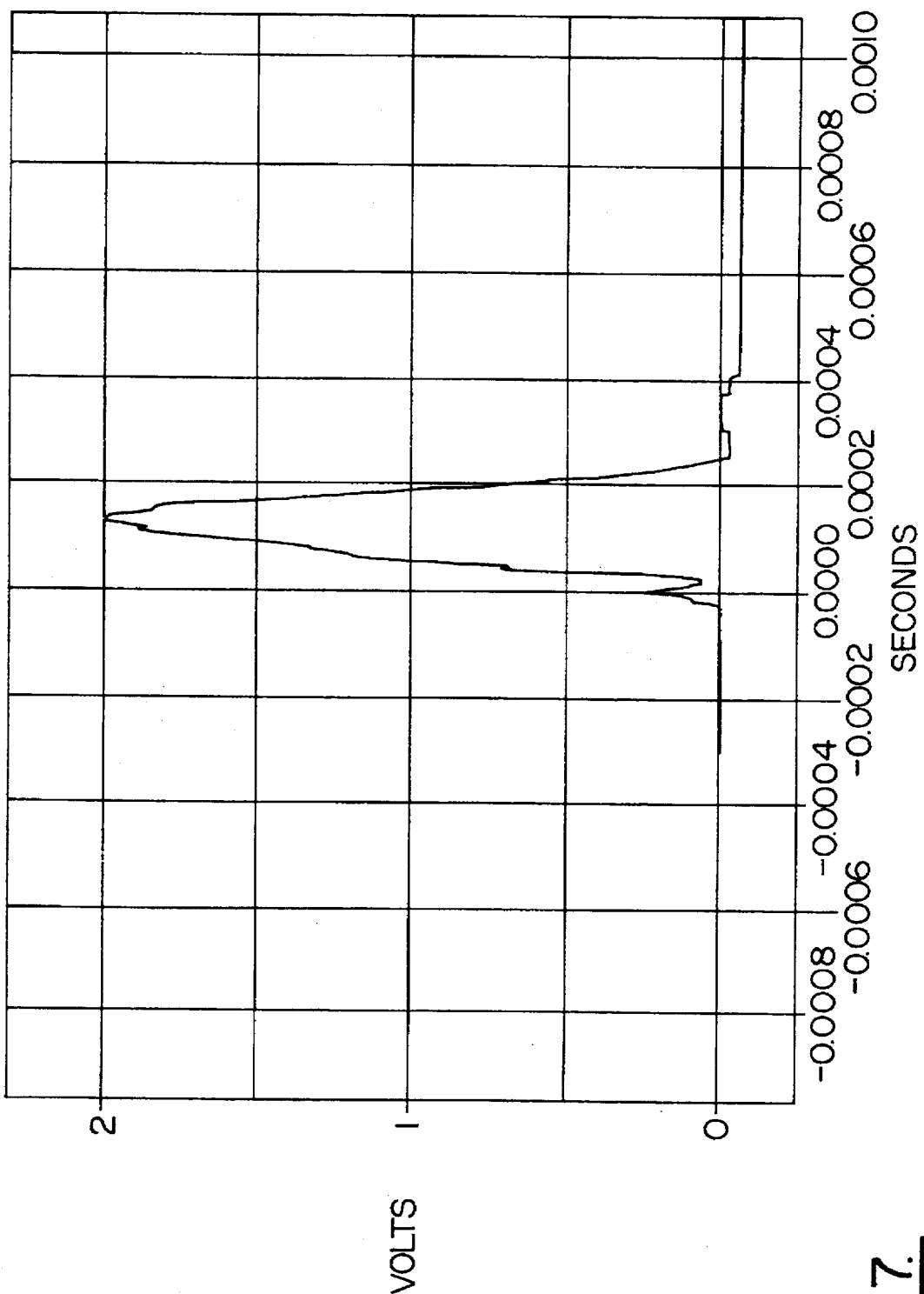
FIG. 7 is a graph indicating loading of the test specimen as a function of time during a specimen test.

The present invention has been reduced to practice using a 40,000 pound load capacity Instron 4507 series testing machine using shear and tension fixtures. FIG. 7 is a digital output of the test specimen load cell 82 measuring load versus time on the test specimen 92 after the failure of the starter specimen 70 in one test. (Load values are obtained by a calibration of the voltage using known loads on the load cell.) The data is recorded using a waveform analyzer, preferably the model Data 6000 manufactured by Data Precision Division, Analogic Corp. The slope of the leading edge of the curve is a measure of the rate of loading, and the maximum value is a measure of the maximum load to which the specimen is subject, which typically is the failure load of the specimen. In this case, loading to failure occurred in about 150 microseconds. By varying the mass of the inertial mass 82, loading rates to failure of from 50 microseconds to 800 microseconds were obtained. A comparison of low rate (i.e., static) vs. high rate loading show an increase of 2 to 2½ times in the joint strength at high loading rates. Thus, the present approach is demonstrated to be controllably operable over a wide range of loading rates. The exact values obtainable depend on the specimen and the type of test fixture assembly.

The present invention thus provides a method of applying a high strain-rate loading that is based upon a loading device that is widely available but otherwise not suitable for high strain-rate loading. The approach is highly versatile, permitting the use of a range of test fixtures and specimens, as well as a wide range of loading rates from quasi-static to impact. Testing is performed quickly, with low cost per specimen tested. Larger numbers of specimens can therefore be tested than with other techniques. The approach is also safe, because the test technician stays well clear of the apparatus during loading and failure of the test specimens.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A test method comprising the steps of:
providing a test apparatus, comprising
an incremental mechanical loading apparatus, the loading apparatus including
an incremental loading apparatus frame having a stationary cross piece and two parallel side supports extending from the stationary cross piece,
a loading head supported between the two side supports and movable in a first direction parallel to the side supports and toward the stationary cross piece, and in a second direction opposite to the first direction, the loading head having a first side facing in the first direction and a second side facing in the second direction,
a starter specimen first grip having a flange engaged to the loading head,
a starter specimen second grip attached to the stationary cross piece,
a test specimen frame supported on the second side of the loading head,
a test specimen first loading fixture engaged to the test specimen frame,
an inertial mass in load-transmitting mechanical communication with the test specimen first loading fixture, and
a test specimen second loading fixture engaged to the inertial mass, the test specimen second loading fixture being disposed such that a test specimen is mountable between the test specimen first loading fixture and the test specimen second loading fixture;
mounting a starter specimen between the starter specimen first grip and the starter specimen second grip;
mounting a test specimen between the test specimen first loading fixture and the test specimen second loading fixture; and
moving the loading head of the incremental mechanical loading apparatus such that the starter specimen is loaded to failure, the failure of the starter specimen causing the application of a force to the test specimen.

2. The test method of claim 1, wherein the step of providing a loading apparatus includes the step of
providing a loading apparatus wherein the side supports include screw drives.

3. The test method of claim 1, wherein the step of providing a loading apparatus includes the step of
providing a starter specimen load cell in one of the starter specimen first grip and the starter specimen second grip.

4. The test method of claim 1, wherein the step of providing a loading apparatus includes the step of
providing a test specimen load cell in one of the test specimen first loading fixture and the test specimen second loading fixture.

5. The test method of claim 1, wherein the step of mounting a starter specimen includes the step of
providing a notched tensile bar as the starter specimen.

6. The test method of claim 1, wherein the step of mounting a test specimen includes the step of
providing a shear test specimen.

7. The test method of claim 1, wherein the step of mounting a test specimen includes the step of
providing a fastener as the test specimen.

8. A test method comprising the steps of:
providing an incremental mechanical loading apparatus having
a loading head movable in a first direction and in a second direction opposite to the first direction, and
a stationary cross piece;
mounting a starter specimen between the loading head and the stationary cross piece, such that the starter specimen extends in the first direction from the loading head and the movement of the loading head in the second direction applies a tensile load to the starter specimen;
mounting a test specimen to the loading head such that the test specimen extends in the second direction from the loading head and such that a mechanical reaction force generated by the breaking of the starter specimen is imparted from the starter specimen to the test specimen; and moving the loading head of the incremental mechanical loading apparatus in the second direction such that the starter specimen is loaded to failure, the failure of the starter specimen causing the application of a force to the test specimen.

9. The test method of claim 8, wherein the step of mounting a remote end of a test specimen includes the step of attaching a test specimen frame to the loading head, the test specimen frame extending in the first direction from the loading head, engaging a remote end of the test specimen to the test specimen frame at a location remote from the loading head, and engaging an inertial mass to an adjacent end of the test specimen at a location between the test specimen and the starter specimen.

10. A test method comprising the steps of:

providing an incremental mechanical loading apparatus having
a loading head movable in a first direction and in a second direction opposite to the first direction, and
a stationary cross piece;

mounting a starter specimen between the loading head and the stationary cross piece, such that the starter specimen extends in the first direction from the loading head and the movement of the loading head in the second direction applies a tensile load to the starter specimen;

mounting a test specimen to the loading head such that a mechanical reaction force generated by the breaking of the starter specimen is imparted from the starter specimen to the test specimen;

placing an inertial mass between the test specimen and the starter specimen such that the mechanical reaction force is imparted into the inertial mass; and moving the loading head of the incremental mechanical loading apparatus in the second direction such that the starter specimen is loaded to failure, the failure of the starter specimen causing the application of a force to the test specimen.

11. A test method comprising the steps of:

providing an incremental mechanical loading apparatus;

mounting an unloaded starter specimen to the loading apparatus in a manner such that the starter specimen is loaded to failure by the operation of the loading apparatus;

mounting a test specimen to the loading apparatus, such that the test specimen is not loaded as the starter specimen is loaded prior to failure of the starter specimen, but such that the test specimen is loaded only after the starter specimen has been loaded to failure; and operating the loading apparatus to load the starter specimen to failure, wherein the test specimen is not loaded prior to failure of the starter specimen but is loaded after the starter specimen has been loaded to failure.

12. The test method of claim 11, wherein the step of providing an incremental mechanical loading apparatus includes the step of providing an incremental mechanical loading apparatus, the loading apparatus including
an incremental loading apparatus frame including a stationary cross piece and two parallel side supports extending from the stationary cross piece, and
a loading head supported between the two side supports and movable in a first direction parallel to the side supports and toward the stationary cross piece, and in a second direction opposite to the first direction.

13. The test method of claim 11, including an additional step of providing instrumentation for the test specimen.

14. The test method of claim 11, wherein the step of providing an incremental mechanical loading apparatus includes the step of providing a movable loading head, and wherein the step of mounting a test specimen includes the step of providing a test specimen frame, and mounting the test specimen frame to the loading head.

15. The test method of claim 14, wherein the step of mounting the test specimen to the loading apparatus includes the step of engaging a remote end of the test specimen to the test specimen frame at a location remote from the loading head, and attaching an adjacent end of the test specimen to an inertial mass.

16. A mechanical loading apparatus comprising:

a loading head movable in first and second opposed directions;

a cross piece spaced from said loading head;

means for mounting a starter specimen between said loading head and said cross piece such that the starter specimen extends in the first direction from said loading head;

means for mounting a test specimen to said loading head such that the test specimen extends in the second direction from said loading head; and means for moving said loading head in the second direction relative to said cross piece such that the starter specimen is loaded to failure, wherein failure of the starter specimen serves to apply a force to the test specimen.

17. A mechanical loading apparatus according to claim 16 wherein said means for mounting the starter specimen comprises:

a starter specimen first grip, operably connected to said loading head, for engaging a first end of the starter specimen; and a starter specimen second grip, operably connected to said cross piece, for engaging a second end of the starter specimen.

18. A mechanical loading apparatus according to claim 16 wherein said means for mounting the test specimen comprises:

a test specimen first loading fixture, operably connected to said loading head, for operably engaging a first end of the test specimen; and a test specimen second loading fixture for operably engaging a second end of the test specimen.

19. A mechanical loading apparatus according to claim 16 further comprising an inertial mass in mechanical communication with the test specimen for increasing the force applied to the test specimen upon failure of the starter specimen.

* * * * *